United States Patent [19]
Park et al.

[11] Patent Number: 5,824,889
[45] Date of Patent: Oct. 20, 1998

[54] CAPACITIVE OIL DETERIORATION AND CONTAMINATION SENSOR

[75] Inventors: Kyong M. Park, Thousand Oaks; Marcos A. Nassar, Los Angeles, both of Calif.

[73] Assignee: Kavlico Corporation, Moorpark, Calif.

[21] Appl. No.: 812,683

[22] Filed: Mar. 6, 1997

[51] Int. Cl.⁶ .................................................. G01M 15/00
[52] U.S. Cl. .............................. 73/116; 701/29; 324/378; 324/382; 324/71.1
[58] Field of Search .................................... 73/116, 117.2, 73/117.3, 118.1, 118.2; 324/378, 382, 71.1; 701/29; 364/424.034

[56] References Cited

U.S. PATENT DOCUMENTS

| | | | |
|---|---|---|---|
| 2,462,715 | 2/1949 | Booth | 177/311 |
| 2,807,956 | 10/1957 | Doble | 73/73 |
| 3,046,537 | 7/1962 | Dow | 340/234 |
| 3,067,385 | 12/1962 | Rykoskey | 324/61 |
| 3,196,667 | 7/1965 | Alquist et al. | 73/53 |
| 3,424,977 | 1/1969 | Krobath | 324/61 |
| 3,522,530 | 8/1970 | Muller | 324/65 |
| 3,523,245 | 8/1970 | Love et al. | 324/61 |
| 3,622,875 | 11/1971 | Bunjiro Ichijo | 324/61 R |
| 3,675,121 | 7/1972 | Thompson | 324/61 R |
| 3,746,974 | 7/1973 | Stoakes et al. | 324/61 R |
| 3,816,811 | 6/1974 | Cmelik | 324/61 R |
| 3,876,916 | 4/1975 | Stoakes | 317/249 R |
| 4,048,844 | 9/1977 | Dunikowski et al. | 73/32 |
| 4,064,455 | 12/1977 | Hopkins et al. | 324/61 R |
| 4,227,419 | 10/1980 | Park | 73/724 |
| 4,345,202 | 8/1982 | Nagy et al. | 324/58.5 B |
| 4,398,426 | 8/1983 | Park et al. | 73/724 |
| 4,468,611 | 8/1984 | Tward | 324/61 R |
| 4,470,300 | 9/1984 | Kobayashi | 73/304 |
| 4,559,493 | 12/1985 | Goldberg et al. | 324/61 R |
| 4,646,070 | 2/1987 | Yasuhara et al. | 340/603 |
| 4,733,556 | 3/1988 | Meitzler et al. | 73/64 |
| 4,806,847 | 2/1989 | Atherton et al. | 324/61 P |
| 4,899,102 | 2/1990 | Hendrick et al. | 324/663 |
| 4,945,863 | 8/1990 | Schmitz et al. | 123/1 A |
| 5,103,184 | 4/1992 | Kapsokavathis et al. | 324/672 |
| 5,125,265 | 6/1992 | O'Connell et al. | 73/61.41 |
| 5,179,926 | 1/1993 | Ament | 123/494 |
| 5,182,523 | 1/1993 | Ertel et al. | 324/663 |
| 5,205,151 | 4/1993 | Shimamura et al. | 73/1 R |

(List continued on next page.)

FOREIGN PATENT DOCUMENTS 0080632  8/1983  European Pat. Off. .

OTHER PUBLICATIONS

Harrison, Dean R. and Dimeff, John; "*Transducers*"; Rev. Sci. Instrum., vol. 44, No. 10, Oct. 1973, pp. 1468–1472.

*Primary Examiner*—George M. Dombroske
*Attorney, Agent, or Firm*—Oppenheimer Wolff & Donnelly LLP

[57] ABSTRACT

An oil deterioration and contamination sensor includes a housing, a substrate with a first capacitive plate mounted within the housing, a second capacitive plate mounted to the housing close to the first capacitive plate, and a total reference capacitor which includes an external fixed reference capacitor. The second capacitive plate is mounted to the housing such that at least one fluid including oil freely circulates within a gap between the first and second capacitive plates thereby defining an oil deterioration and contamination sensor capacitor. The respective capacitances of the oil deterioration and contamination capacitor and the total reference capacitor provide an indication of a dielectric constant of the at least one fluid including oil within the gap. The sensor also includes circuitry for generating the indication of a dielectric constant and oil contamination detection circuitry adapted to receive and process the indication of a dielectric constant and to generate an indication of oil contamination when a dielectric constant of the at least one fluid including oil exceeds a predetermined value or exceeds a predetermined value at a rate of dielectric constant change in excess of a maximum ordinary rate of oil dielectric constant change.

18 Claims, 5 Drawing Sheets

U.S. PATENT DOCUMENTS

| | | | |
|---|---|---|---|
| 5,261,270 | 11/1993 | Gonze et al. | 73/61.43 |
| 5,262,732 | 11/1993 | Dickert et al. | 324/672 |
| 5,274,335 | 12/1993 | Wang et al. | 324/689 |
| 5,281,922 | 1/1994 | Lofgren et al. | 324/684 |
| 5,283,711 | 2/1994 | Schmitz | 361/286 |
| 5,284,056 | 2/1994 | Randolph et al. | 73/440 |
| 5,309,110 | 5/1994 | O'Neill et al. | 324/674 |
| 5,313,168 | 5/1994 | Ogawa | 324/663 |
| 5,331,845 | 7/1994 | Bal et al. | 73/61.43 |
| 5,337,017 | 8/1994 | Ogawa | 324/682 |
| 5,367,264 | 11/1994 | Brabetz | 324/674 |
| 5,418,465 | 5/1995 | Seipler et al. | 324/663 |
| 5,435,170 | 7/1995 | Voelker et al. | 73/53.05 |
| 5,488,311 | 1/1996 | Kamioka et al. | 324/674 |
| 5,540,086 | 7/1996 | Park et al. | 73/53.05 |
| 5,604,441 | 2/1997 | Freese, V et al. | 324/663 |

CAPACITIVE OIL DETERIORATION AND CONTAMINATION SENSOR

BACKGROUND OF THE INVENTION

1. Field of the Invention

The present invention relates to an oil deterioration and contamination sensor and, more particularly, pertains to a sensor employing a capacitive transducer with an oil deterioration and contamination sensor capacitor, at least one reference capacitor and electronics for distinguishing between oil deterioration and contamination.

2. Description of the Related Art

One of the most important factors that contributes to the efficiency and durability of internal combustion engines is lubrication. As engine oil "breaks down" it is less effective in protecting an engine from damage caused by friction between engine parts. More specifically, the normal life span of motor oils is limited by thermal breakdown, additive depletion and carbon particulates that result from the combustion process.

The deterioration of engine oil is marked by a decrease in the viscosity of the oil. The dielectric constant of engine oil provides an indication of the oil's deterioration or lack thereof. The dielectric constant of motor oil is typically between 1.6 and 3.2 depending upon its brand and age. For example, the dielectric constant of a particular brand of motor oil may increase from 2.19 to 2.35 after 400 hours of use in a particular internal combustion engine under certain operating conditions. Thus, it is desirable to have a means for indicating when engine oil has deteriorated to the point where it should be changed.

Premature lubrication failure can also result from the presence of contaminants in the engine oil such as coolant (glycol ethylene), fuel or water. The presence of these contaminants in motor oil is often indicative of a mechanical failure such as a damaged head gasket or a broken piston ring. Thus, it is also desirable to have a means for detecting the presence of these substances in engine oil.

Water and engine coolant have dielectric constants of approximately 87.5 and 37.0, respectively. Therefore, the introduction of such a contaminant into the engine oil significantly increases the dielectric constant of some of the fluid which circulates through the engine for the purpose of lubrication. As a result, a condition of engine oil contamination could be mistaken for severe engine oil deterioration or vice versa.

The dielectric constant of oil is also influenced by the temperature of the oil and by the specific formulation of a given brand of oil.

Accordingly, an object of the present invention is to provide an oil deterioration and contamination sensor employing a capacitive transducer wherein the engine oil is utilized as a dielectric medium.

Another object is provide an oil deterioration and contamination sensor which distinguishes between the conditions of engine oil deterioration and contamination and provides separate indications of these conditions.

Another object is to provide an oil deterioration and contamination sensor which utilizes a combination of fixed and variable capacitors to provide an indication of engine oil breakdown for a wide variety of engine oil formulations.

Another object is to provide an oil deterioration and contamination sensor wherein the variable capacitances are configured such that stray capacitances are reduced.

Another object is to provide an oil deterioration and contamination sensor which adjusts the engine oil deterioration measurements to compensate for the effects of engine oil temperature changes.

SUMMARY OF THE INVENTION

In accordance with a specific illustrative embodiment of the present invention, an oil deterioration and contamination sensor includes a housing, a substrate with a first capacitive plate mounted within the housing, a second capacitive plate mounted to the housing close to the first capacitive plate, and a total reference capacitor which includes an external fixed reference capacitor. The second capacitive plate is mounted to the housing such that at least one fluid including oil freely circulates within a gap between the first and second capacitive plates thereby defining an oil deterioration and contamination sensor capacitor. The respective capacitances of the oil deterioration and contamination capacitor and the total reference capacitor provide an indication of the dielectric constant of the at least one fluid including oil within the gap.

In a further aspect of the present invention, the capacitive oil deterioration and contamination sensor also includes: circuitry for generating the indication of dielectric constant utilizing the capacitances of the oil deterioration and contamination sensor capacitor and the total reference capacitor; and oil contamination detection circuitry adapted to receive and process the indication of dielectric constant and to generate an indication of oil contamination when the dielectric constant of the at least one fluid including oil exceeds a predetermined value or exceeds a predetermined value at a rate of dielectric constant change in excess of a maximum ordinary rate of oil dielectric constant change.

In a further aspect of the present invention, the first capacitive plate is divided into a major sensing area, and a minor sensing area covering a relatively small portion of the total area of the first capacitive plate. The major sensing area and the second capacitive plate form the oil deterioration and contamination sensor capacitor. The total reference capacitor further includes an oil deterioration and contamination reference capacitor defined by the minor reference area and the second capacitive plate.

In still another aspect of the present invention, the oil deterioration and contamination sensor further includes a temperature sensitive resistive element thermally connected to the substrate for providing a temperature adjustment to the indication of dielectric constant, and circuitry utilizing the respective capacitances of the oil deterioration and contamination sensor capacitor and the total reference capacitor to generate the indication of dielectric constant.

In accordance with another aspect of the invention, the oil deterioration and contamination sensor may include a threaded metal housing with an inner end for extending into the oil pan of an engine, with the two capacitive plates being mounted at the inner end and being open and spaced apart for the free flow of oil between the capacitive plates.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein.

DETAILED DESCRIPTION OF THE PREFERRED EMBODIMENTS

Figure 1:
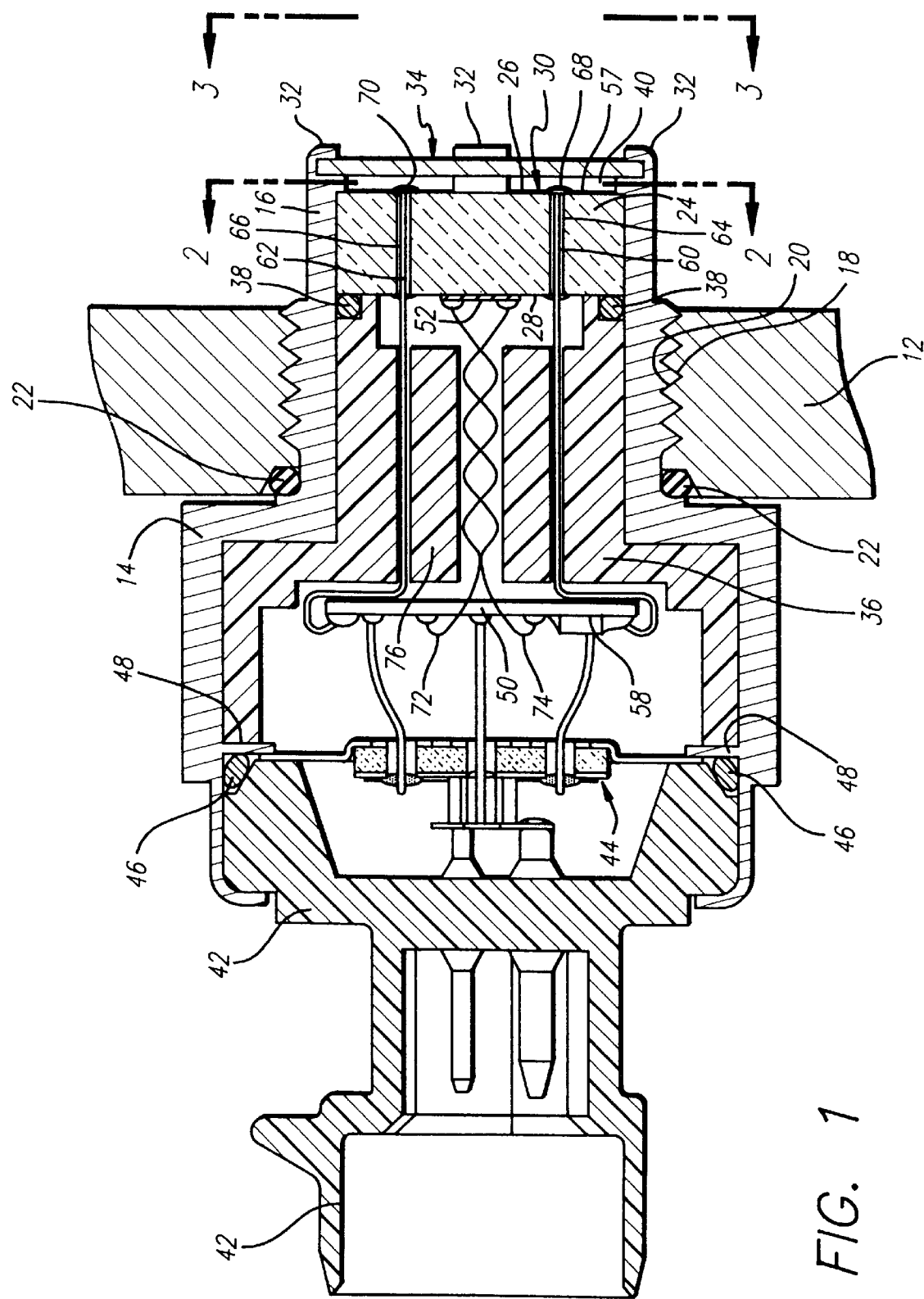
FIG. 1 is a cross-sectional side view of an oil deterioration and contamination sensor of the present invention.

FIG. 1 is a cross-sectional side view of a capacitive oil deterioration and contamination sensor 10 fitted within a wall 12 of an engine oil reservoir, such as the oil pan of a motorized vehicle. The sensor 10 includes a metal housing 14 with an inner end 16 which extends into the oil pan and is exposed to the oil therein. The inner end 16 preferably includes a threaded surface portion 18 which is fitted within a corresponding threaded bore 20 of the oil pan wall 12. A circular gasket 22 made of a sealant such as rubber may also be positioned between the housing 14 and the wall 12 as shown in FIG. 1. The wall 12 may be a thick local area in a thinner metal oil pan to provide additional strength for receiving the oil deterioration sensor.

The housing 14, and particularly the inner end 16, are precisely machined to receive a substrate 24. The preferred inner end 16 is sized to form a cylindrical chamber along the length of the sensor 10. Accordingly, the preferred substrate 24 is cylindrical in shape with an outer diameter (e.g., 0.6 in.) slightly less than the inner diameter of the inner end 16. The substrate 24 is preferably manufactured from an insulating material which efficiently conducts heat. For example, the substrate 24 may be formed from a ceramic material such as alumina.

The substrate 24 includes an outer surface 26 and an inner surface 28 on opposing sides thereof, with the substrate 24 being oriented within the inner end 16 such that the outer surface 26 faces the interior of the oil pan. A first capacitive plate 30 is formed on the outer surface 26 and is exposed to the engine oil. The first capacitive plate 30 is formed from a conductive material. In a preferred embodiment, the plate 30 is comprised of gold and may have a thickness of one or two thousandths of an inch. It may be silk screened on to the ceramic disk 24 in paste form and fired.

The inner end 16 of the housing 14 additionally includes a plurality of supports 32 which are sized to secure a second capacitive plate 34 within the housing 14. The second capacitive plate 34 is also made from a conductive material (e.g., steel), and is held stationary by the supports 32 such that the first 30 and second 34 capacitive plates are substantially parallel. The distance between the first 30 and second 34 plates is preferably between 0.010 and 0.020 inches to permit the free circulation of oil from the oil pan through the space between the plates.

The oil deterioration and contamination sensor 10 additionally includes means for preventing the substrate 24 from sliding within the inner end 16 away from the second capacitive plate 34. For example, the preventing means may comprise an outer spacer 36 fitted within the housing 14. Also, a ring seal 38 may be provided to prevent the engine oil from seeping past the substrate 24 and into the housing 14. The ring seal 38 is comprised of a sealant such as silicone rubber.

The four supports 32, in addition to securing the second capacitive plate 34 to the housing 14, are spaced apart around the inner end 16 such that engine oil freely circulates within a gap 40 between the first capacitive plate 30 and the second capacitive plate 34. Accordingly, an oil deterioration and contamination sensor capacitor is defined by the first capacitive plate 30, the second capacitive plate 34 and the engine oil in the gap 36. The capacitance of the oil deterioration and contamination sensor capacitor varies depending upon the dielectric constant of the oil between the plates 30 and 34.

Before the operational aspects of the capacitive oil deterioration and contamination sensor 10 are discussed in detail, it should be noted that the sensor 10 additionally includes a connector shell portion 42 which is mechanically connected to the housing 14 as shown in FIG. 1. A plurality of connectors or conductive terminals are secured within the shell portion 42. A connector support structure 44 and a ring seal 46 are secured between a conductive retaining ring 48 and the connector shell portion 42. The retaining ring 48, in turn, is secured between the support structure 44 and the ring seal 46 on one side and the outer spacer 36 on the other side. The aforedescribed mechanical assembly prevents the structure 24, and thus the first capacitive plate 30, from sliding within the housing 14, relative to the second capacitive plate 34.

The oil deterioration and contamination sensor 10 further includes circuitry within the housing 14 for generating an indication of engine oil dielectric constant and an engine oil deterioration indication signal. Preferably, some of the elements of the circuitry are provided in an integrated circuit 50 (e.g., a hybrid integrated circuit) which is thermally isolated from the substrate 24. The circuitry also includes the oil deterioration and contamination sensor capacitor and a total reference capacitor (discussed below). In a preferred embodiment, the circuitry also includes other circuit elements which are necessarily in thermal contact with the substrate 24. For example, the circuitry also includes a temperature sensitive resistor 52 which is mechanically attached or bonded to the inner surface 28 and thermally connected to the substrate 24.

Figure 2:
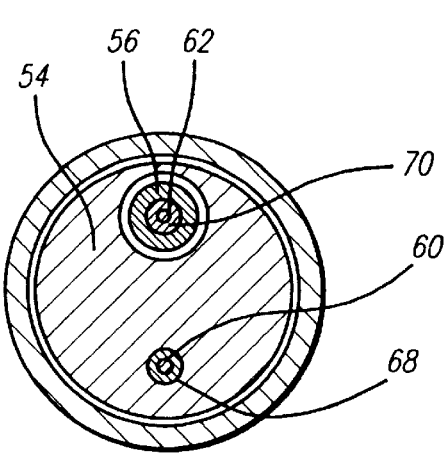
FIG. 2 is an end view of the oil deterioration and contamination sensor along the 2—2 line of FIG. 1.

FIG. 2 is an end view of the oil deterioration and contamination sensor 10 along the 2—2 line of FIG. 1. The first capacitive plate 30 is divided into a major sensing area 54, and a minor reference area 56 covering a relatively small fraction of a total area of the first capacitive plate 30. The major sensing area 54 and the second capacitive plate 34 form the oil deterioration sensor capacitor ($C_e$) with the engine oil serving as the dielectric material therebetween. The sensor 10 may also include a passivation layer 57 formed over the first capacitive plate 30. For example, the passivation layer 57 may comprise a polyamide coating between 0.0005 and 0.002 inch in thickness.

The total reference capacitor ($C_R$) mentioned supra includes an external fixed reference capacitor ($C_{RF}$) 58 (FIG. 1) which is electrically connected to the integrated circuit 50. The total reference capacitor further includes an oil deterioration reference capacitor ($C_{Re}$) which is electrically connected in parallel with $C_{RF}$. The oil deterioration and contamination reference capacitor ($C_{Re}$) is defined by the minor reference area 56 and the second capacitive plate 34 with the engine oil also serving as the dielectric material therebetween. The plate 34 and the housing 14 may be formed of steel, and may be at ground potential. Accordingly, the following formula approximates the relationship between the above reference capacitors:

$$C_R = C_{RF} + C_{R\epsilon}$$

The preferred major sensing area 54 is 0.188 in.$^2$ and may be generally circular in shape. The preferred minor reference area 56 is positioned within and electrically isolated from the major sensing area 54, 0.015 in.$^2$ and generally circular in shape. As shown in FIG. 1, the major sensing area 54 and the minor reference area 56 are electrically connected to the integrated circuit 50 by leads 60, 62, respectively.

During assembly of the oil deterioration and contamination sensor 10, leads 60, 62 are respectively routed through conduits 64, 66 which are formed in the substrate 24. The conduits 64,66 are sized only slightly larger than the leads 60, 62 so that a sealant need not be injected or otherwise positioned between the leads 60,62 and inner walls of the conduits 64, 66. FIG. 2 further illustrates that the lead 60 is electrically connected to the major sensing area 54 by a solder joint 68. Similarly, the lead 62 is electrically connected to the minor reference area 56 by a solder joint 70. Solder joints 68, 70 may include silver epoxy (e.g., Heraeus 60-193) and additionally act to prevent engine oil from seeping into the sensor 10 through the conduits 64, 66.

FIG. 1 illustrates that the second capacitive plate 34 is electrically connected to the integrated circuit 50 through the electrically conductive housing 14, retaining ring 48 and connector support structure 44. Also, the temperature sensitive resistor 52 is electrically connected to the integrated circuit 50 by leads 72, 74 which are preferably isolated from the leads 60, 62 by an inner insulating plastic spacer 76.

Figure 3:
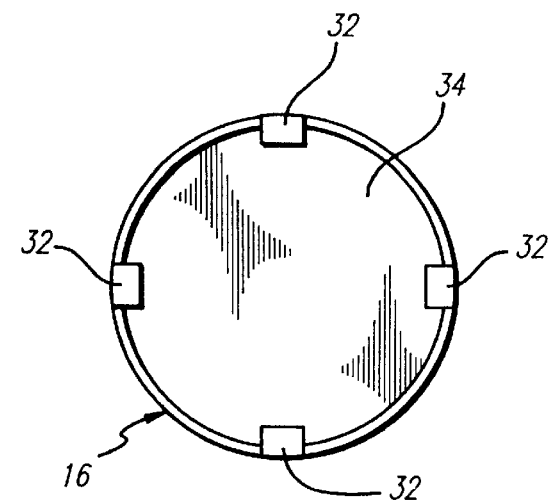
FIG. 3 is an end view of the oil deterioration and contamination sensor along the 3—3 line of FIG. 1.

FIG. 3 is a limited end view of the oil deterioration and contamination sensor 10 along the 3—3 line of FIG. 1. The second capacitive plate 34 is shown secured by four supports 32 which are evenly spaced around the inner end 16. As may be readily appreciated, the plurality of supports 32 may comprise a number other than four supports and are not necessarily evenly spaced around the inner end 16. In fact, any configuration of supports 32 which allows the free flow of engine oil into the gap 40 is contemplated.

Figure 4:
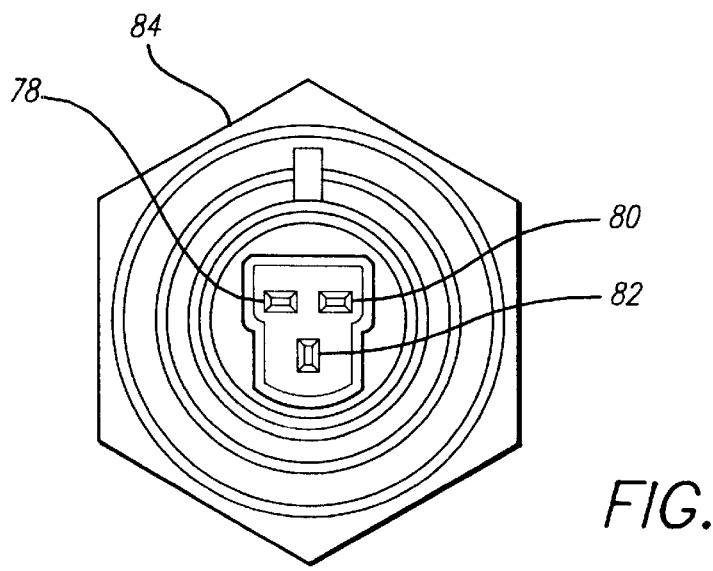
FIG. 4 is a rear view of the oil deterioration and contamination sensor of FIG. 1.

FIG. 4 is a rear view of the oil deterioration and contamination sensor 10 of FIG. 1. The terminals supported by the connector shell portion 42 include a ground voltage terminal 78, a supply voltage terminal 80 and an output voltage terminal 82. The operating supply voltage ($V_{cc}$) applied across terminals 80, 78 and thereby supplied to the circuitry is 5.000±0.250 VDC. The engine oil deterioration indication signal ($V_{OUT}$) generated by the circuitry is measured across terminals 82, 78 at the connector shell portion 42.

A preferred shell portion 42 includes a hexagonal exterior surface 84 which permits a mechanic, vehicle owner, etc. to thread the oil deterioration and contamination sensor 10 into or out of the oil pan bore 20 as desired with a conventional wrench. Other mechanical structures facilitating the mounting and insertion of the sensor 10 into the oil pan of an engine are also contemplated.

Figure 5:
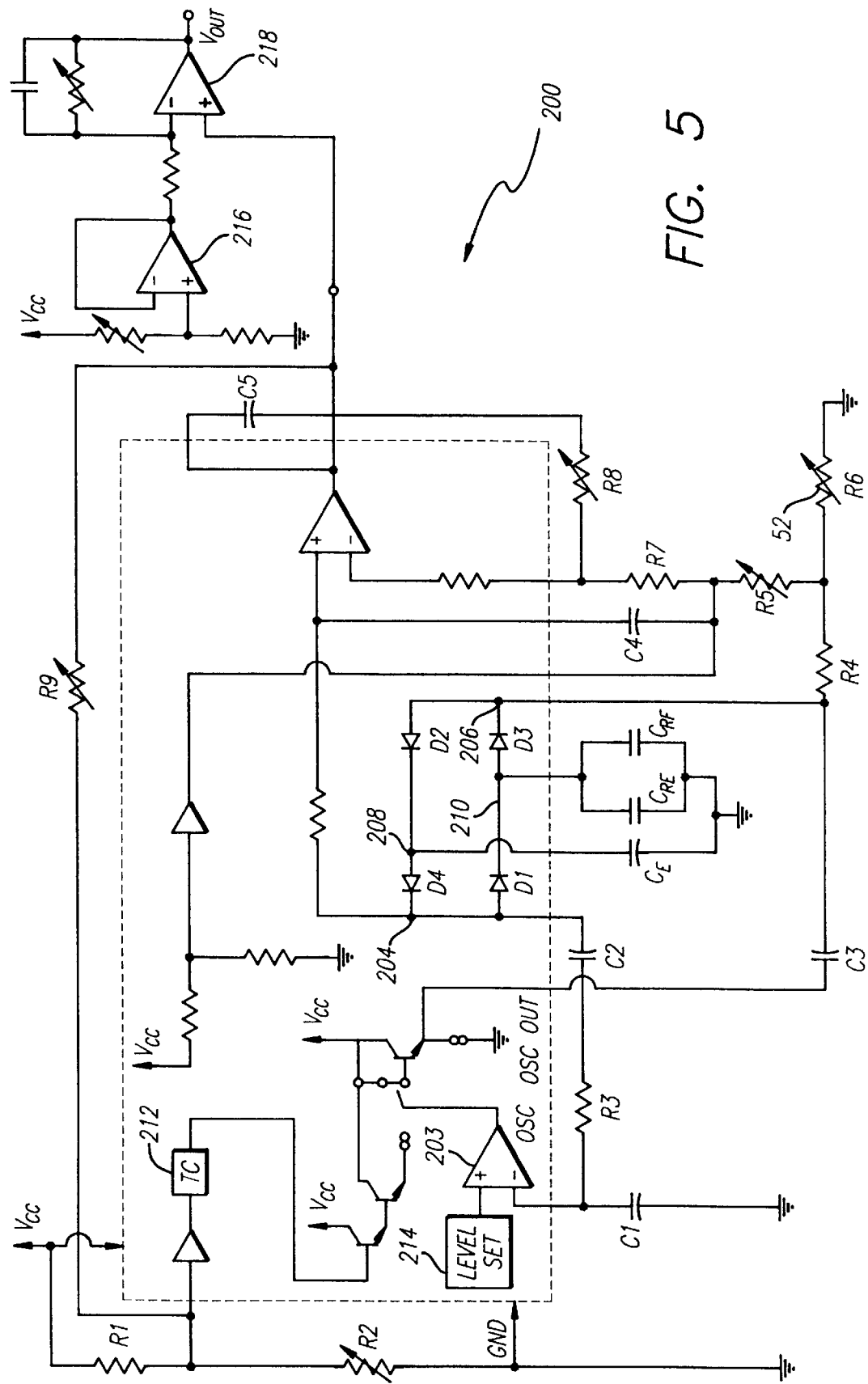
FIG. 5 is an electrical schematic of circuitry within the oil deterioration and contamination sensor for generating an indication of engine oil viscosity.

FIG. 5 is an electrical schematic of circuitry 200 within the oil deterioration sensor 10 for generating an indication of engine oil dielectric constant and, more particularly, the engine oil deterioration indication signal ($V_{OUT}$) For the purpose of simplification, the operating supply voltage ($V_{cc}$) and a ground (GND) are generally shown as being provided to the hybrid 50. As may be readily appreciated, the dashed-line boundary of the hybrid 50 may be adjusted as circuit elements are either added to or relocated externally from the hybrid 50.

Generally, a capacitive transducer must be excited by an alternating current (AC) carrier voltage. Demodulating electronics are also needed to generate a direct current (DC) output. Accordingly, the circuitry 200 includes a diode-quad circuit 202 which is excited by a AC carrier voltage provided by an oscillator (OSC) 203. The diode-quad circuit 202 further includes diodes D1, D2, D3 and D4 arranged to form nodes 204, 206, 208, 210 as shown in FIG. 5. More specifically, the anode of D1 and the cathode of D4 are electrically connected at the node 204, the anode of D2 and the cathode of D3 are electrically connected at the node 206, the cathode of D2 and the anode of D4 are electrically connected at the node 208, and the cathode of D1 and the anode of D3 are electrically connected at the node 210.

The engine oil deterioration indication signal ($V_{OUT}$) is generated by the circuitry 200 and is described by the following formula:

$$V_{OUT} \propto (C_\epsilon - C_R)/(C_\epsilon + C_R)$$

The oil deterioration and contamination sensor capacitor ($C_{68}$) is electrically connected across the node 208 and GND. The total reference capacitor ($C_R$), which as discussed above comprises the oil deterioration and contamination reference capacitor ($C_{R\epsilon}$) in parallel with external fixed reference capacitor ($C_{RF}$), is electrically connected across the node 210 and GND. Since the capacitors $C_{68}$, $C_{R\epsilon}$, and $C_{RF}$ are not included within the hybrid 50, they are shown outside the dashed-line outlining the hybrid 50.

The oil deterioration and contamination reference capacitor ($C_{R\epsilon}$) is used to minimize the differences between the respective dielectric breakdown characteristics of various motor oil formulations. The capacitance of $C_{RF}$ is chosen such that $C_\epsilon$ is approximately equal to $C_R$ when fresh motor oil is introduced into the gap 40. The capacitance of $C_{68}$ is 5–15 pF without motor oil in the gap 40 and 6–20 pF when the gap 40 is filled with fresh motor oil.

After the motor oil begins to break down, the respective capacitances of $C_\epsilon$ and $C_R$ both change, with $C_\epsilon$ being more sensitive to changes in the dielectric constant of the motor oil than $C_R$. As described above, it has been observed that the engine oil deterioration indication signal ($V_{OUT}$) is proportional to $(C_\epsilon - C_R)/(C_\epsilon + C_R)$. In summary, the circuitry 200 utilizes the respective capacitances of $C_\epsilon$ and $C_R$ to generate $V_{OUT}$.

As shown in FIG. 5, the preferred circuitry 200 also includes a temperature compensation element 212 and a level set 214 for the oscillator 203. These additional elements are conventional with the temperature compensation element 212 regulating the output of the oscillator 203 under changing environmental conditions. Further with regard to temperature compensation, the temperature sensitive resistor 52 is designated as R6 and adjusts $V_{OUT}$ to compensate for changes in $V_{OUT}$ caused by changes in the temperature of the engine oil. The preferred temperature sensitive resistor 52 (FIG. 1) is a resistive paste sold under the name Sensohm manufactured by Ferro Corporation of 27 Castillian Drive, Santa Barbara, Calif. 93117-3092. Sensohm is characterized as providing 10 KΩ/unit with the resistor 52 being formed on the substrate 24 with an appropriate amount of Sensohm to measure 36 KΩ. Following application to the substrate as a paste, the resistor 52 is fired to bond it to the inner surface 28 of the disk 24.

The preferred circuitry 200 further includes an external offset circuit 216 and an external gain circuit 218 which receive and adjust the output of the diode-quad circuit 202 as required to provide $V_{OUT}$. The aforedescribed signal conditioning may also be provided by alternative embodiments of the circuitry 200. For example, an alternative embodiment of the circuitry may include diode-quad circuits such as those described in "Transducers" by Dean R. Harrison and John Dimeff, Rev. Sci. Instrum., Vol. 44, No. 10, October 1973 which is herein incorporated by reference. Other circuits such as those disclosed in U.S. Pat. Nos. 4,227,419 and 4,398,426, assigned to the assignee of this invention, may also be employed.

Figure 6:
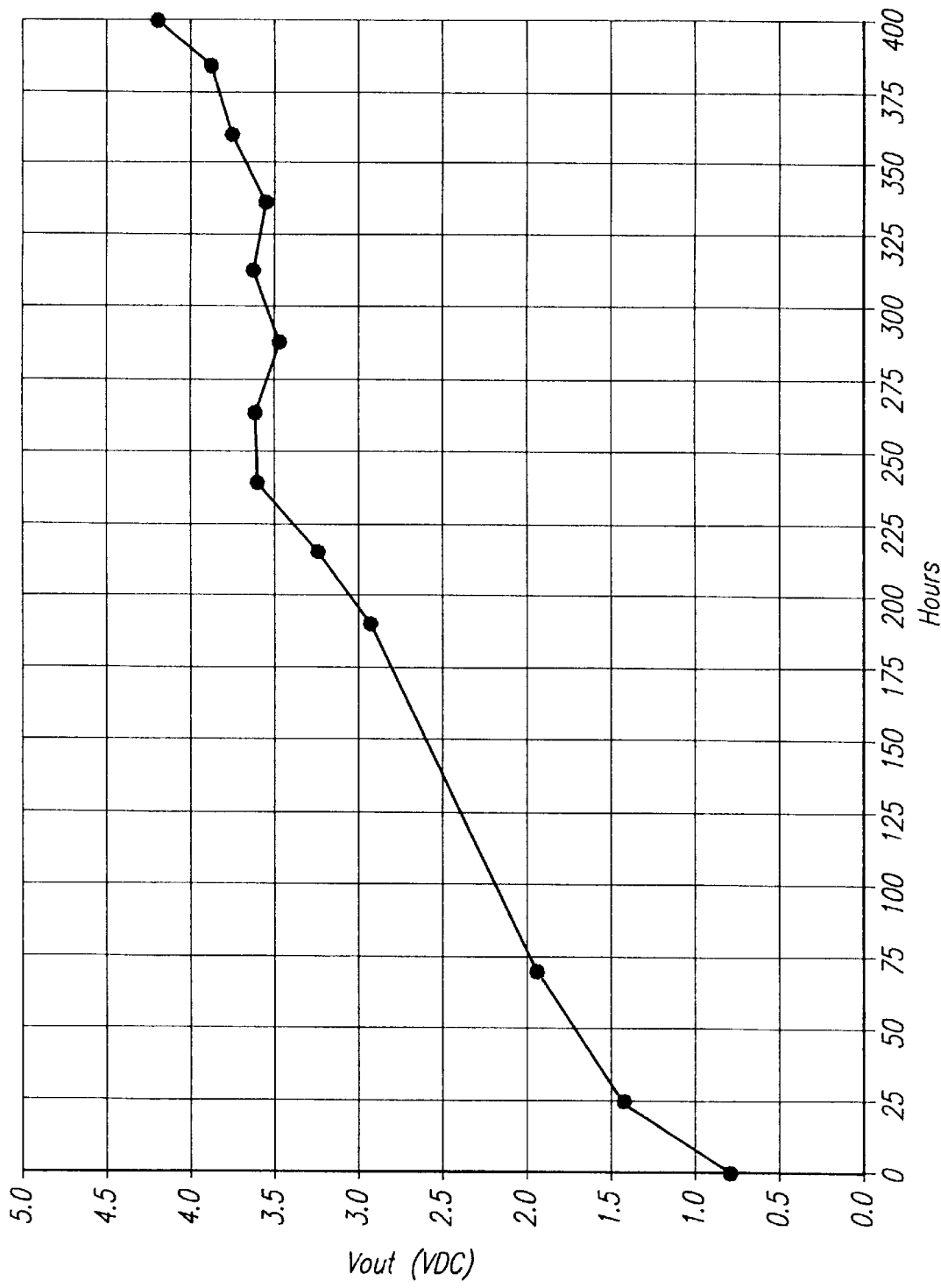
FIG. 6 is a plot of an output voltage (VDC) of the sensor at room temperature over time (hours) showing deterioration of the engine oil under test over time.

FIG. 6 is a plot of the sensor's output indication voltage (VDC) at room temperature over time (hours) of operation of an internal combustion engine. Since capacitance across parallel plates is generally described by the equation $$C = \epsilon (A/d),$$

the respective capacitances of $C_\epsilon$ and $C_{R\epsilon}$ are substantially governed by the above equation wherein $\epsilon$ is the dielectric constant of the motor oil within the gap 40. Since the dielectric constant of motor oil increases as the oil breaks down, the plot of FIG. 6 demonstrates that $V_{OUT}$ is proportional to $(C_\epsilon - C_R)/(C_\epsilon + C_R)$. As discussed above, the capacitance of $C_{RF}$ is chosen such that $C_\epsilon$ is approximately equal to $C_R$ when fresh motor oil is introduced into the gap 40 so that the engine oil deterioration indication signal ($V_{OUT}$) initially generated by the circuitry 200 measures close to 0.0 VDC. As the motor continues to run and the oil therein breaks down, it has been observed that $V_{OUT}$ increases over time as shown in FIG. 6.

Figure 7:
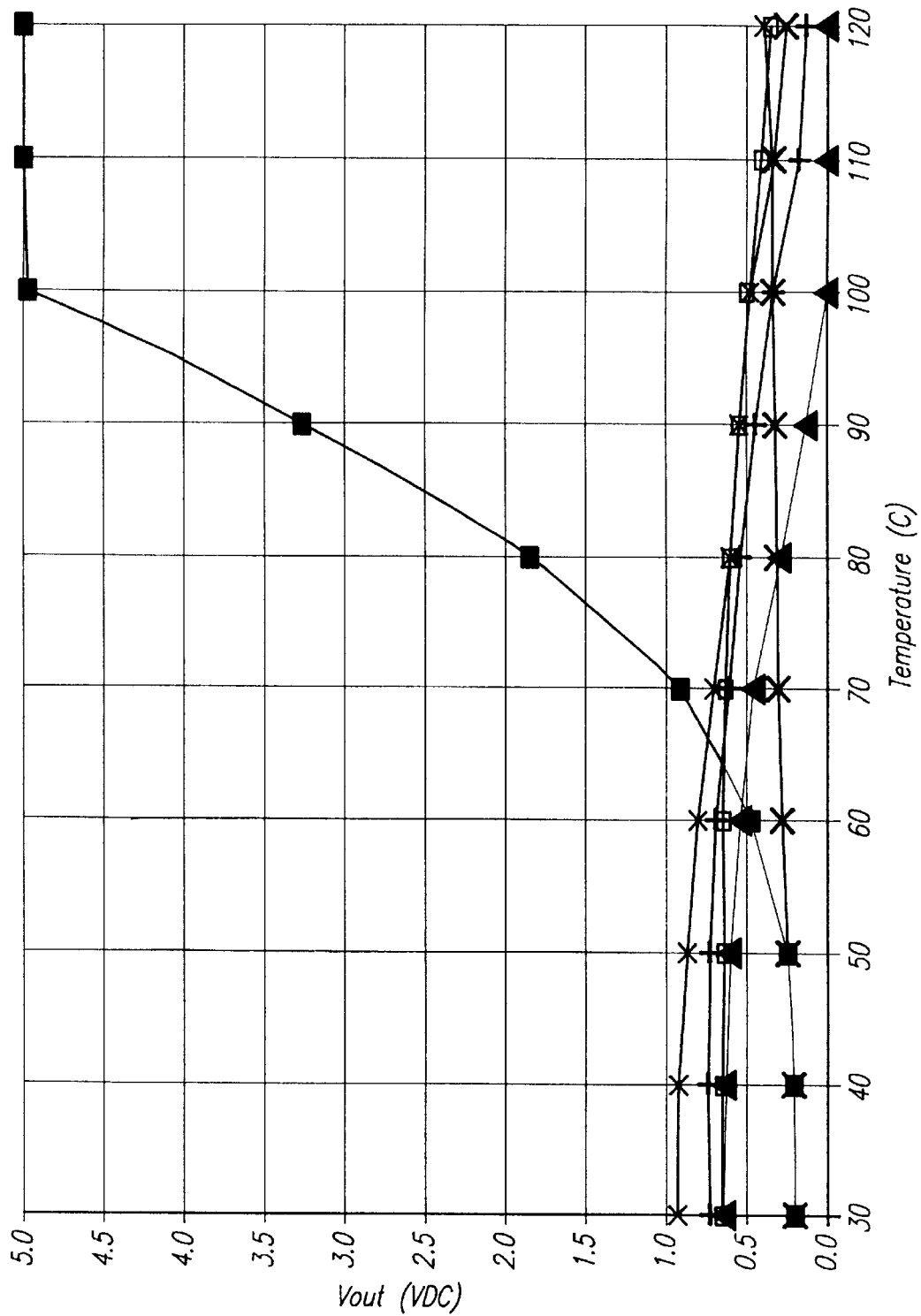
FIG. 7 is a plot of the output voltage (VDC) for various engine oil formulations over temperature (°C)

FIG. 7 is a plot of $V_{OUT}$ for various engine oil formulations over engine oil temperature. The data points corresponding to each particular engine oil formulation are respectively represented by a different type of indicia. The following table shows which indicia correspond to each of the tested engine oil formulations.

| Brand | Indicia |
|-------|---------|
| A | ■ |
| B | □ |
| C | + |
| D | × |
| E | * |
| F | ▲ |

$V_{OUT}$ for each of the tested formulations was observed to increase or decrease over temperature without the adjustment provided by the temperature sensitive resistor 52. As may be readily appreciated, the resistor 52 is particularly useful in accommodating most of the tested engine oil formulations where the temperature effects were observed to be substantially linear in nature. Brand B through F were well known nationally distributed brands of motor oil, which Brand A was a cheap local unknown brand. It is believed that one of the chemical additions in Brand A caused the unusual characteristic shown for plot A.

A key aspect of the present invention is the inclusion of additional circuitry to distinguish between conditions of engine oil deterioration and contamination and to provide a separate indication of the latter condition.

Figure 8:
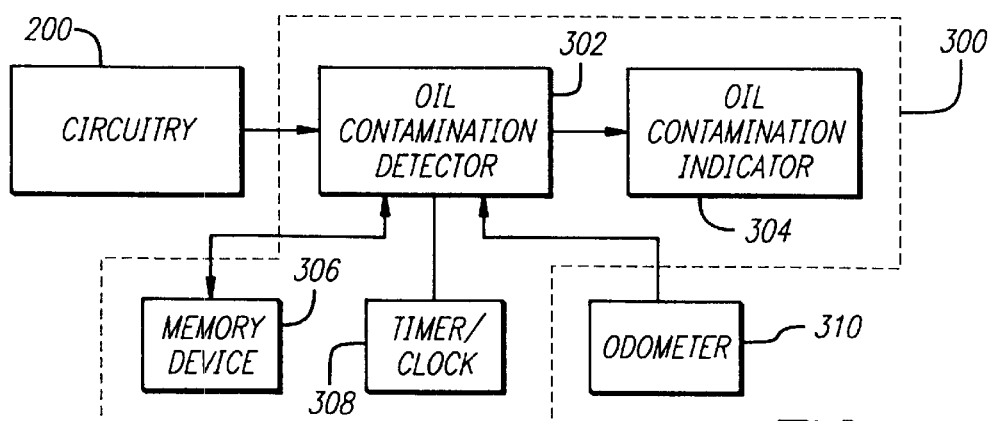
FIG. 8 is a functional block diagram showing circuitry for providing an indication of dielectric constant and oil contamination detection circuitry.

As shown in FIG. 8, oil contamination detection circuitry 300 is electrically connected to the circuitry 200 and receives the indication of dielectric constant therefrom. As may be readily appreciated, the oil contamination detection circuitry 300 can be embodied within or external to the hybrid 50. The oil contamination detection circuitry 300 includes an oil contamination detector 302, an oil contamination indicator 304, a memory device 306 and a timer/clock 308. The oil contamination detector 302 includes a conventional processor which is programmed to receive and process input signals from the circuitry 200, the memory device 306, the timer/clock 308 and an odometer 310. The oil contamination indicator 304 comprises, for example, a warning light on the dash of a vehicle, and is actuated by a signal provided from the oil contamination detector 302. Other sensors or devices may also provide inputs to the oil contamination detector 302.

The indication of dielectric constant from the circuitry 200 is stored in the memory device 306 and regularly updated under control of the oil contamination detector 302. The program executed by the oil contamination detector 302 employs output signals generated by the timer/clock 308 and/or the odometer 310 and is thereby able to distinguish between engine oil deterioration which typically is associated with a higher dielectric constant than uncontaminated but deteriorated motor oil and occurs gradually and engine oil contamination which typically occurs suddenly due to the failure of a mechanical part or the inadvertent introduction of a contaminant into the engine oil. Thus, if the dielectric constant reaches a relatively high value, for example above 5 or 8, the oil contamination detection circuitry 300 will provide an indication of oil contamination regardless of timing or mileage input.

Accordingly, the oil contamination detector 302 is programmed in consideration of the fact that motor oil contamination typically causes a drastic change in the dielectric constant of fluids circulating within the engine for the purpose of lubrication. The program executed by the oil contamination detector 302 is also preferably implemented in consideration of the immiscible nature of engine oil and contaminants such as engine coolant and water. Without the oil contamination circuitry 300, a high voltage or saturated output from the circuitry 200 could be construed as an indication of either severe motor oil deterioration or contamination.

In conclusion, it is to be understood that the foregoing detailed description and the accompanying drawings illustrate the principles of the invention. However, various changes and modifications may be employed without departing from the spirit and scope of the invention. Thus, by way of example and not of limitation, the housing could be formed of a high strength engineered plastic instead of steel, and the second capacitive plate could be in the form of a coating on the inside of an insulating plate, with suitable electrical connections to the hybrid circuit being provided. Also instead of the ceramic disk 24 the inner capacitive plate could be formed as a separate metallic plate, electrically isolated from the facing plate and from the housing if the housing is metallic; and the temperature sensitive resistor could be mounted on the opposite surface of this plate, electrically isolated by a thin electrically insulating but thermally conductive layer. Other mechanical and electrical changes of a comparable nature could also be made. Accordingly, the present invention is not limited to the specific form shown in the drawings and described in detail hereinabove.

What is claimed is:

1. A capacitive oil deterioration and contamination sensor comprising:

a threaded metal housing having an inner end for threading into an oil pan of an automobile or other engine, said inner end including supports attached thereto;

a heat-conducting substrate mounted within said inner end and insulated from said housing, said substrate including an inner surface and an outer surface and a first capacitive plate on said outer surface;

a second capacitive plate mounted to said housing by said supports close to but apart from said first capacitive plate such that at least one fluid including oil freely circulates within a gap between said first and second capacitive plates, said first and second capacitive plates defining an oil deterioration and contamination sensor capacitor;

a total reference capacitor including an external fixed reference capacitor, said oil deterioration and contamination sensor capacitor and said total reference capacitor providing an indication of a dielectric constant of said at least one fluid including oil within said gap;

circuitry for generating said indication of a dielectric constant utilizing capacitances of said oil deterioration and contamination sensor capacitor and said total reference capacitor;

a temperature sensitive resistive element thermally connected to said inner surface of said substrate for providing a temperature adjustment to said indication of a dielectric constant in response to a temperature of said at least one fluid including oil; and oil contamination detection circuitry adapted to receive and process said indication of a dielectric constant and to generate an indication of oil contamination when a dielectric constant of said at least one fluid including oil exceeds a predetermined value at a rate of dielectric constant change in excess of a maximum ordinary rate of oil dielectric constant change.

2. A capacitive oil deterioration and contamination sensor comprising:

a threaded metal housing having an inner end for threading into an oil pan of an automobile or other engine, said inner end including supports attached thereto;

a heat-conducting substrate mounted within said inner end and insulated from said housing, said substrate including an inner surface and an outer surface and a first capacitive plate on said outer surface;

a second capacitive plate mounted to said housing by said supports close to but apart from said first capacitive plate such that at least one fluid including oil freely circulates within a gap between said first and second capacitive plates, said first and second capacitive plates defining an oil deterioration and contamination sensor capacitor;

a total reference capacitor including an external fixed reference capacitor, said oil deterioration and contamination sensor capacitor and said total reference capacitor providing an indication of a dielectric constant of said at least one fluid including oil within said gap;

a temperature sensitive resistive element thermally connected to said inner surface of said substrate for providing a temperature adjustment to said indication of a dielectric constant in response to a temperature of said at least one fluid including oil; and oil contamination detection circuitry adapted to receive and process said indication of a dielectric constant and to generate an indication of oil contamination when a dielectric constant of said at least one fluid including oil exceeds a predetermined value at a rate of dielectric constant change in excess of a maximum ordinary rate of oil dielectric constant change.

3. The capacitive oil deterioration sensor of claim 2 wherein said first capacitive plate is divided into a major sensing area, and a minor reference area covering a relatively small fraction of a total area of said first capacitive plate, said major sensing area and said second capacitive plate forming said oil deterioration and contamination sensor capacitor, said total reference capacitor further including an oil deterioration and contamination reference capacitor defined by said minor reference area and said second capacitive plate.

4. The capacitive oil deterioration and contamination sensor of claim 2 further comprising:

circuitry for generating said indication of a dielectric constant utilizing capacitances of said oil deterioration and contamination sensor capacitor and said total reference capacitor.

5. The capacitive oil deterioration and contamination sensor of claim 2 further comprising:

a temperature sensitive resistive element thermally connected to said substrate for providing a temperature adjustment to said indication of a dielectric constant in response to a temperature of said at least one fluid including oil.

6. The capacitive oil deterioration and contamination sensor of claim 2 wherein said substrate comprises a ceramic material.

7. The capacitive oil deterioration and contamination sensor of claim 2 further comprising:

a glass passivation layer over said first capacitive plate.

8. The capacitive oil deterioration and contamination sensor of claim 2 wherein a distance between said first and second capacitive plates is between 0.010 and 0.020 inches.

9. The capacitive oil deterioration and contamination sensor of claim 2 wherein said first capacitive plate is substantially parallel to said second capacitive plate.

10. A capacitive oil deterioration and contamination sensor comprising:

a threaded metal housing having an inner end for protruding into an oil pan of an automobile or other engine;

an exposed insulating disk having a first metal capacitive plate on an outer surface thereof insulated from said housing and mounted within said inner end of said housing;

a second metal capacitive plate spaced close to but apart from said first metal capacitive plate for cooperation with said first metal capacitive plate;

supports for mounting said second metal capacitive plate to permit free circulation of at least one fluid including oil between said first and second metal capacitive plates;

a temperature sensitive resistance mounted on an inner surface of said insulating disk on another side of said insulating disk from said first metal capacitive plate; and means for detecting changes in a dielectric constant of said at least one fluid including oil circulating between said plates and for providing an indication when said dielectric constant is greater than or equal to a predetermined value at a rate of dielectric constant change in excess of a maximum ordinary rate of oil dielectric constant change.

11. The capacitive oil deterioration and contamination sensor of claim 10 wherein said insulating disk comprises a ceramic material which rapidly transfers heat to said temperature sensitive resistance.

12. The capacitive oil deterioration and contamination sensor of claim 10 wherein said first metal capacitive plate is divided into a major sensing area, and a minor reference area covering a relatively small fraction of a total area of said first metal capacitive plate, an external reference capacitor is provided, and circuitry is employed to combine a capacitance of said external reference capacitor with a capacitance of said minor reference area to provide a total reference capacitance and to compare said total reference capacitance to a capacitance of said major sensing area.

13. A capacitive oil deterioration and contamination sensor comprising:

a housing having an inner end for protruding into an oil pan of an automobile or other engine;

a substrate mounted within said inner end and insulated from said housing, said substrate including a first capacitive plate on an outer surface of said substrate;

a second capacitive plate mounted to said housing close to but apart from said first capacitive plate such that at least one fluid including oil freely circulates within a gap between said first and second capacitive plates, said first and second capacitive plates defining an oil deterioration and contamination sensor capacitor;

a total reference capacitor including an external fixed reference capacitor, said oil deterioration and contamination sensor capacitor and said total reference capacitor providing an indication of a dielectric constant of said at least one fluid including oil within said gap; and oil contamination detection circuitry adapted to receive and process said indication of a dielectric constant and to generate an indication of oil contamination when a dielectric constant of said at least one fluid including oil exceeds a predetermined value at a rate of dielectric constant change in excess of a maximum ordinary rate of oil dielectric constant change.

14. The capacitive oil deterioration and contamination sensor of claim 13 wherein said first capacitive plate is divided into a major sensing area, and a minor reference area covering a relatively small fraction of a total area of said first capacitive plate, said major sensing area and said second capacitive plate forming said oil deterioration and contamination sensor capacitor, said total reference capacitor further including an oil deterioration and contamination reference capacitor defined by said minor reference area and said second capacitive plate.

15. The capacitive oil deterioration and contamination sensor of claim 13 further comprising:

circuitry for generating said indication of a dielectric constant utilizing capacitances of said oil deterioration and contamination sensor capacitor and said total reference capacitor.

16. The capacitive oil deterioration and contamination sensor of claim 13 further comprising:

a temperature sensitive resistive element thermally connected to said substrate for providing a temperature adjustment to said indication of a dielectric constant in response to a temperature of said at least one fluid including oil.

17. The capacitive oil deterioration and contamination sensor of claim 13 wherein said substrate comprises a ceramic material.

18. The capacitive oil deterioration and contamination sensor of claim 13 further comprising a glass passivation layer over said first capacitive plate.

* * * * *